(12) United States Patent
Nielsen

(10) Patent No.: US 9,707,175 B2
(45) Date of Patent: Jul. 18, 2017

(54) CHEWING GUM COMPOSITION COMPRISING CROSS-LINKED POLYACRYLIC ACID

(75) Inventor: Bruno Provstgaard Nielsen, Vejle (DK)

(73) Assignee: FERTIN PHARMA A/S (DK)

( * ) Notice: Subject to any disclaimer, the term of this patent is extended or adjusted under 35 U.S.C. 154(b) by 8 days.

(21) Appl. No.: 13/996,877

(22) PCT Filed: Dec. 21, 2010

(86) PCT No.: PCT/DK2010/000181
§ 371 (c)(1),
(2), (4) Date: Jun. 21, 2013

(87) PCT Pub. No.: WO2012/083947
PCT Pub. Date: Jun. 28, 2012

(65) Prior Publication Data
US 2013/0280179 A1    Oct. 24, 2013

(51) Int. Cl.
| | |
|---|---|
| *A61K 9/68* | (2006.01) |
| *A23G 4/06* | (2006.01) |
| *A23G 4/08* | (2006.01) |
| *A61K 31/465* | (2006.01) |
| *A61K 47/32* | (2006.01) |
| *A61K 47/48* | (2006.01) |

(52) U.S. Cl.
CPC .............. *A61K 9/0058* (2013.01); *A23G 4/06* (2013.01); *A23G 4/08* (2013.01); *A61K 31/465* (2013.01); *A61K 47/32* (2013.01); *A61K 47/48184* (2013.01)

(58) Field of Classification Search
None
See application file for complete search history.

(56) References Cited

U.S. PATENT DOCUMENTS

| | | | | |
|---|---|---|---|---|
| 3,901,248 | A * | 8/1975 | Lichtneckert et al. ....... | 131/359 |
| 5,227,154 | A | 7/1993 | Reynolds | |
| 5,300,305 | A | 4/1994 | Stapler et al. | |
| 5,378,131 | A | 1/1995 | Greenberg | |
| 6,001,344 | A * | 12/1999 | Villa et al. ................ | 424/78.02 |
| 6,238,689 | B1 * | 5/2001 | Rhodes et al. .............. | 424/436 |
| 6,471,945 | B2 | 10/2002 | Luo et al. | |
| 6,479,071 | B2 | 11/2002 | Holme et al. | |
| 6,485,739 | B2 | 11/2002 | Luo et al. | |
| 6,627,234 | B1 | 9/2003 | Johnson et al. | |
| 6,685,916 | B1 | 2/2004 | Holme et al. | |
| 6,696,044 | B2 | 2/2004 | Luo et al. | |
| 6,733,818 | B2 | 5/2004 | Luo et al. | |
| 6,846,500 | B1 | 1/2005 | Luo et al. | |
| 2003/0099741 | A1 | 5/2003 | Gubler | |
| 2003/0157213 | A1 | 8/2003 | Jenkins | |
| 2003/0206993 | A1 | 11/2003 | Gubler | |
| 2003/0215417 | A1 | 11/2003 | Uchiyama et al. | |
| 2004/0081713 | A1 | 4/2004 | Maxwell et al. | |
| 2004/0136928 | A1 | 7/2004 | Holme et al. | |
| 2005/0008732 | A1 | 1/2005 | Gebreselassie et al. | |
| 2005/0025721 | A1 | 2/2005 | Holme et al. | |
| 2005/0123502 | A1 * | 6/2005 | Chan ................... | A61K 31/4439 424/78.3 |
| 2006/0099300 | A1 * | 5/2006 | Andersen et al. ................ | 426/3 |
| 2006/0153949 | A1 * | 7/2006 | Gebreselassie .......... | A23G 4/06 426/3 |

FOREIGN PATENT DOCUMENTS

| | | | | |
|---|---|---|---|---|
| DK | WO 2009080022 A1 * | 7/2009 | .......... | A61K 9/0058 |
| WO | 9600070 A1 | 1/1996 | | |
| WO | WO 2010069311 A1 * | 6/2010 | | |

OTHER PUBLICATIONS

MSDS from Spectrum Chemical Corp, downloaded Dec. 29, 2014 from https://www.spectrumchemical.com/MSDS/N5712.PDF.*
Seong Hoon Jeong and Kinam Park. Drug loading and release properties of ion-exchange resin complexes as a drug delivery matrix. International journal of Pharmaceutics 361 (2008) 26-32.*
Jed E. Rose. "Nicotine Replacement Therapies and Other Nicotinic Strategies", Chapter 4 of Medication Treatments for Nicotine Dependence, Edited by Tony George. Boca Raton, FL: CRC Press, 2007, pp. 63-65.*
International Search Report Application No. PCT/DK2010/000181 Completed: Sep. 9, 2011; Mailing Date: Sep. 20, 2011 2 pages.

* cited by examiner

*Primary Examiner* — Isaac Shomer
*Assistant Examiner* — Michael P Cohen
(74) *Attorney, Agent, or Firm* — St. Onge Steward Johnston and Reens, LLC

(57) ABSTRACT

The present invention provides a chewing gum composition comprising a gum base matrix and a bulk portion, wherein the chewing gum composition comprises nicotine and includes a cross-linked polyacrylic acid, such as a carbomer, added in an amount of 0.1 to 5.0% by weight of the chewing gum composition. The invention may be used to enhance the release of nicotine in a nicotine chewing gum.

36 Claims, No Drawings

CHEWING GUM COMPOSITION COMPRISING CROSS-LINKED POLYACRYLIC ACID

FIELD OF THE INVENTION

The present invention relates to the field of chewing gum. In particular the present invention relates to the use of a cross-linked polyacrylic acid in chewing gum compositions. The invention may be used to enhance the release of nicotine in a nicotine chewing gum.

BACKGROUND

A traditional way of producing a nicotine chewing gum is to add the nicotine in complex with a cation exchange resin and incorporate this complex into a chewing gum formulation.

U.S. Pat. No. 3,901,248 discloses a chewable smoking substitute composition with a cation exchange resin complex dispersed in the base. Although the release of nicotine is controlled and thus allowing most of the initially added amount of nicotine to be released from the chewing gum formulation during a predetermined time period, the release of nicotine from the chewing gum formulation does not resemble the instant release of nicotine from a cigarette.

SUMMARY OF THE INVENTION

Accordingly, there is provided a chewing gum composition comprising a gum base matrix and a bulk portion, wherein the chewing gum composition includes a cross-linked polyacrylic acid added in an amount of 0.1 to 5.0% by weight of the chewing gum composition.

Furthermore, there is provided a method of producing a chewing composition with the cross-linked polyacrylic acid comprising the steps of providing a gum base matrix and a bulk portion, and adding a cross-linked polyacrylic acid as part of the bulk portion after mixing the gum base matrix.

Furthermore, there is provided a method of enhancing the release of nicotine in a chewing gum comprising the cross-linked polyacrylic acid.

Furthermore, there is provided a method of enhancing the release of active ingredients in a chewing gum comprising the cross-linked polyacrylic acid.

DETAILED DESCRIPTION

Surprisingly, it has been seen that the addition of a cross-linked polyacrylic acid, such as a carbomer, in an amount of 0.1 to 5.0% by weight of the chewing gum composition provides several important advantages compared to the prior art.

One of the advantages of the present invention is that the addition of cross-linked polyacrylic acid, such as a carbomer, may enhance the release of nicotine significantly compared to the prior art.

According to one aspect of the invention there is provided a chewing gum composition comprising a gum base matrix and a bulk portion, wherein the chewing gum composition comprises nicotine and includes a cross-linked polyacrylic acid added in an amount of 0.1 to 5.0% by weight of the chewing gum composition.

The increased release of nicotine from the chewing gum composition is highly unexpected and solves a long felt need in the field of nicotine chewing gum.

Ever since the first nicotine chewing gum products were launched on the market, it has been the goal to obtain the same instant effects as may be seen when smoking a cigarette. However, it is believed that there has been a prejudice to allow for an instant release of nicotine from a chewing gum. This has mainly been reasoned by the fact that chewing gum comprises a hydrophobic gum base which is traditionally believed to slow the release of nicotine.

Cross-linked polyacrylic acid has also been known from the pharmaceutical industry to slow the release of active ingredients. In particular cross-linked polyacrylic acids, such as carbomers, have been used in lozenges as binders in order to delay the release of active ingredients from the tablet. Furthermore, cross-linked polyacrylic acids, such as carbomers, have been used in lozenges as mucoadhesives in order to delay the absorption of active ingredients through the oral mucosa.

The inventors of the present invention have found the opposite effect in chewing gum, namely an increased release of active ingredients, such as nicotine, after adding cross-linked polyacrylic acid, such as a carbomer, to the chewing gum formulation, which is contrary to every expectation.

Although cross-linked polyacrylic acid, such as a carbomer, has the benefit of being hydrophobic in nature and therefore being compatible with the hydrophobic nature of traditional chewing gum base, it was not at all expected that the release of active ingredients, such as nicotine, may be increased by adding the cross-linked polyacrylic acid to the chewing gum composition.

Without being bound by theory it is believed that the cross-linked nature of the polyacrylic acid according to the invention is necessary to obtain the benefits of the present invention. The cross-linked nature is believed to allow for increased water uptake during chewing of the chewing gum, whereby it is believed that an increased amount of the active ingredient, such as nicotine, is released from the chewing gum composition, while still maintaining the cross-linked polyacrylic acid as part of the chewing gum matrix during chewing.

Another advantage of the invention is that an enhanced texture is obtained according to the invention. The cross-linked nature is believed to allow for increased water uptake during chewing of the chewing gum, while still maintaining the cross-linked polyacrylic acid as part of the chewing gum matrix during chewing. In the present context this effect may be measured as an increased volume of the chewing gum matrix after chewing compared to a situation where no cross-linked polyacrylic acid is added. This technical effect solves the problem of small chewing gum matrices after extensive chewing, and thus provides an increased volume of the chewing gum matrix after extensive chewing.

Since a high amount of active ingredients, such as nicotine, is traditionally retained in the chewing gum formulation even after pronounced mastication, the direct impact of the invention in terms of economical benefit is that a lower amount of active ingredients, such as nicotine, may be necessary to give the same amount of release of active ingredient or to give the same craving relief when nicotine is used.

To the surprise of the inventors of the present invention, it was realised that the stability of the final chewing gum formulation was at an acceptable level when using the cross-linked polyacrylic acid according to the invention compared to a formulation without the cross-linked polyacrylic acid.

In addition, the invention may in another aspect be used to enhance the degradation of degradable chewing gum having a gum base matrix with an environmentally degradable gum base polymer. In this context it is believed that the increased water uptake during chewing of the chewing gum according to the invention promotes degradation after the chewing gum lump has been chewed and deposited under environmental conditions.

As used herein, the term "chewing gum formulation" intends to mean all chewable gum products.

The term "in vitro chewing" intends to mean that the chewing gum system is chewed according to Ph. Eur. 2.9.25 in a pH 7.4 phosphate buffer with 60 chews per minute and at a temperature of 37° C.

The term such as "enhanced release" or "increased release" or "improved release" is herein intended to mean that the amount of the active ingredient released from the chewing gum formulation according to the invention over time in an in vitro set-up as defined in the present context is higher than the amount of the active ingredients released from the chewing gum formulation over time when cross-linked polyacrylic acid has not been added to the chewing gum formulation.

The term "gum base matrix" intends to mean the mainly insoluble gum base ingredients that are mixed together before the bulk portion of the chewing gum formulation is added.

The term "bulk portion" intends to mean the mainly soluble chewing gum ingredients that are mixed into the gum base matrix after it has been mixed.

The term "weight of the chewing gum formulation" or similar wording meaning the same is defined in the present context as weight of the chewing gum formulation, without including the weight of an outer coating, such as a hard coating, soft coating, and the like.

By the phrase "chewing gum" is meant any chewing gum such as extruded chewing gum, centre-filled chewing gum, toffee-imitating chewing gum, compressed chewing gum, slabs or sticks.

By the term "carbomer" is usually meant high weight polymers of acrylic acid that are cross-linked with either allyl sucrose or allyl ethers of pentaerythritol, typically containing between 52 and 68% carboxylic acid groups calculated on the dry basis.

By the term "polycarbophil" is usually meant high weight acrylic acid polymer cross-linked with divinyl glycol.

In the present context the term "stable" means stable according to ICH guidelines, i.e. at least 18 months when the primary packed product is stored in a climate chamber at a temperature of 25° C. and a relative humidity of 60%.

The amount of cross-linked polyacrylic acid is important according to the invention. When a too high amount of cross-linked polyacrylic acid is used, the chewing gum base may disintegrate. This may in particular be seen in amounts higher than 5.0% of cross-linked polyacrylic acid by weight of the chewing gum formulation, but is also dependent on the actual composition of the gum base matrix and the bulk portion of the chewing gum composition When a too low amount of cross-linked polyacrylic acid is used, the benefit of the invention is not so pronounced. However, as low as 0.1% by weight of cross-linked polyacrylic acid may give a technical effect.

In some embodiments of the invention the optimal effect of the invention is seen when using an amount of cross-linked polyacrylic acid from 0.1 to 5.0% by weight of the chewing gum formulation.

One of the perspectives of the present invention is that it is possible to design the release of an active ingredient, such as nicotine, by the amount of cross-linked polyacrylic acid that is added to the chewing gum formulation. In some situations it may be desirable to have an instant release of the active ingredient, such as nicotine, at the onset of mastication. In some other situations it may be desirable to have a release of the active ingredient, such as nicotine, that allows for a predetermined relief of the active ingredient to the patient in need thereof.

In some embodiments of the invention the cross-linked polyacrylic acid is added in powder form.

In some preferred embodiments of the invention the cross-linked polyacrylic acid is added as part of the bulk portion after mixing of the gum base matrix. It has been seen that the release of the active ingredient, such as nicotine, may be enhanced by adding the cross-linked polyacrylic acid as part of the bulk portion after mixing of the gum base matrix. In some other embodiments of the invention the cross-linked polyacrylic acid is added as part of the components in the gum base matrix, although it is presently comtemplated that the best release effect is seen when adding the cross-linked polyacrylic acid as part of the bulk portion.

In some embodiments the cross-linked polyacrylic acid is added in an amount of 0.1 to 4.5% by weight of the chewing gum composition.

In some embodiments the cross-linked polyacrylic acid is added in an amount of 0.2 to 4% by weight of the chewing gum composition.

In some embodiments the cross-linked polyacrylic acid is added in an amount of 0.5 to 3.5% by weight of the chewing gum composition.

In some embodiments the cross-linked polyacrylic acid is added in an amount of 0.5 to 3.0% by weight of the chewing gum composition.

In some embodiments the cross-linked polyacrylic acid is added in an amount of 0.5 to 2.5% by weight of the chewing gum composition.

According to the invention, the addition of the cross-linked polyacrylic acid may improve the release of nicotine from the chewing gum composition.

In some embodiments of the invention the percentage of released nicotine after 10 min. in vitro chewing in accordance with Ph. Eur. 2.9.25 in a pH 7.4 phosphate buffer with 60 chews per minute and at a temperature of 37° C. is at least 50% of the initially added content.

In some embodiments of the invention the percentage of released nicotine after 10 min. in vitro chewing in accordance with Ph. Eur. 2.9.25 in a pH 7.4 phosphate buffer with 60 chews per minute and at a temperature of 37° C. is at least 60% of the initially added content.

In some embodiments of the invention the percentage of released nicotine after 10 min. in vitro chewing in accordance with Ph. Eur. 2.9.25 in a pH 7.4 phosphate buffer with 60 chews per minute and at a temperature of 37° C. is at least 70% of the initially added content.

In some embodiments of the invention the percentage of released nicotine after 10 min. in vitro chewing in accordance with Ph. Eur. 2.9.25 in a pH 7.4 phosphate buffer with 60 chews per minute and at a temperature of 37° C. is at least 80% of the initially added content.

According to the invention, the gum base matrix may constitute 50 to 80% by weight of the chewing gum composition. The amount of gum base may in some embodiments constitute 60 to 70% by weight of the chewing gum composition. The amount of gum base is considered to have an impact on the release of the active ingredient, such as nicotine. A high amount of gum base may in principle delay the release of the active ingredient, such as nicotine, while a low amount of gum base may enhance the release of the active ingredient, such as nicotine.

According to other embodiments of the invention, the gum base matrix may constitute 20 to 50% by weight of the chewing gum composition. The amount of gum base may in some embodiments constitute 30 to 40% by weight of the chewing gum composition.

In some embodiments of the invention the cross-linked polyacrylic acid is a polycarbophil.

In some embodiments of the invention the cross-linked polyacrylic acid is a carbomer.

In some embodiments of the invention, the carbomer is selected from the group consisting of Carbomer 934, Carbomer 971, Carbomer 974 and mixtures thereof.

In some embodiments of the invention, the carbomer is Carbomer 934. In some embodiments of the invention, the carbomer is Carbomer 971. In some embodiments of the invention, the carbomer is Carbomer 974.

In some embodiments of the invention, the cross-linked polyacrylic acid forms a carrier to the nicotine.

Although the presently preferred embodiment of the invention is to add the cross-linked polyacrylic acid separate from the active ingredient, it may in some embodiments be preferred to use the cross-linked polyacrylic acid as a carrier for the active ingredient, such as nicotine. The acidic nature of the cross-linked polyacrylic acid may in particular be advantageous as a substrate for nicotine in its ionic form. It is believed that a complex between nicotine and cross-linked polyacrylic acid is stable and provides particular advantageous effects in terms of release properties as compared to the prior art.

In some embodiments of the invention, the nicotine is reversible bound to the cross-linked polyacrylic acid. The reversibility may resemble the traditionally used nicotine polacrilex resin.

Cationic ion exchange resins are well known in the art and the present invention encompasses all of these. A preferred cation exchange resin is a methacrylic, weakly acidic type of resin containing carboxylic functional groups. Representative cation exchange resins suitable for use in accordance with the present invention are disclosed in U.S. Pat. No. 3,901,248. The preferred cation exchange resins are those known in the art as the Amberlite® resins from Rohm and Haas, Paris, Cedex, France and include, for example, Amberlite® IR20, Amberlite® IRP69, Amberlite® IRP64, Amberlite® IRP58, Amberlite® IRC50, and Amberlite® IRP69. Preferred cation exchange resins are polacrilex ion exchange resin (Amberlite® IRP64) and a weak acidic exchange resin Purolite C115HMR from Purolite.

In one embodiment of the invention the cation exchange resin is selected from the group consisting of (i) a methacrylic, weakly acidic type of resin containing carboxylic functional groups such as polacrilex (Amberlite® IRP64) (ii) a polystyrene, strongly acidic type of resin containing sulphonic functional groups, and (iii) a polystyrene, intermediate acidic type of resin containing phosphonic functional groups.

In some embodiments of the invention, the nicotine is selected from the group consisting of a nicotine salt, the free base form of nicotine, a nicotine derivative, such as a nicotine cation exchanger, such as nicotine polacrilex resin, a nicotine inclusion complex or nicotine in any non-covalent binding; nicotine bound to zeolites; nicotine bound to cellulose, such as microcrystalline, or starch microspheres, and mixtures thereof.

In a preferred embodiment of the invention, the nicotine includes a nicotine polacrilex resin.

In some embodiments of the invention, the nicotine includes a nicotine salt, such as a nicotine bitartrate In some embodiments of the invention, the nicotine includes a nicotine base.

In one embodiment of the invention the active ingredient is nicotine in any form.

In some embodiments of the invention, nicotine is included in a strength of 1.0 to 5.0 mg.

Usually nicotine chewing gum is provided in two strengths, one of 2 mg and one of 4 mg.

In some embodiments of the invention, the addition of cross-linked polyacrylic acid to the chewing gum composition implies that a lower amount of nicotine may be used to deliver the required dose of nicotine to the patient in need thereof.

In some embodiments of the invention, nicotine is included in a strength of 0.5 to 1.5 mg.

In some embodiments of the invention, a buffer is added, the buffer being selected from the group consisting of a tris buffers, amino acid buffers, carbonate, including monocarbonate, bicarbonate or sesquicarbonate, glycerinate, phosphate, glycerophosphate, acetate, glyconate or citrate of an alkali metal, such as potassium and sodium, e.g. trisodium and tripotassium citrate, or ammonium, and mixtures thereof.

When buffer is used, the preferred buffer is sodium bicarbonate. In some embodiments buffer is not part of the chewing gum formulation. This may for instance be the case when nicotine is present in its base form. In some other embodiments, buffer is part of the chewing gum formulation. This may for instance be the case when nicotine is present in form of a salt or in its ionic form.

In some embodiments of the invention buffer is used together with nicotine polacrilex resin.

Without being bound by theory it is believed that the binding of water by cross-linked polyacrylic acid may give rise to a more pronounced buffer effect and then in turn an enhanced release of nicotine form the chewing gum formulation. This may in particular be seen when using nicotine in the form of nicotine polacrilex resin.

In some embodiments of the invention, the amount of buffer is 0.5 to 10% by weight of the chewing gum composition.

It is contemplated that the pH in a human subject is different from subject to subject. Accordingly, some subjects may have a pH in the oral cavity which is lower than other subjects. Therefore, the increase in pH value will depend on the subject in question, which in turn makes the distinction of an absolute pH value not so meaningful than the relative pH value, such as an increase in pH units.

In some embodiments of the invention the gum base matrix comprises a first amount of buffer from 2 to 20 percent by weight of the gum base matrix. In these embodiments agglomeration is avoided or limited to a low degree.

In general the pH value of the saliva in a human subject is just below 7. In some embodiments of the invention a pH value above 8.0 is important to obtain conditions in the oral cavity for better oral hygiene. A pH above 8.0 is believed to prevent caries and lessen the symptoms of gingivitis, or other disorders in the oral cavity. In some other embodiments a pH above 8.0 is believed to lessen symptoms of acidic conditions in the stomach of a human subject. In some further embodiments a pH above 8.0 supports the release of additional ingredients in the chewing gum formulation, such as active ingredient, such as active pharmaceutical ingredients, such as nicotine.

In some embodiments of the invention the buffer is selected from the group consisting of a carbonate, including monocarbonate, bicarbonate or sesquicarbonate, glycerinate, phosphate, glycerophosphate, acetate, glyconate or citrate of an alkali metal, such as potassium and sodium, e.g. trisodium and tripotassium citrate, or ammonium, tris buffer, amino acids, and mixtures thereof.

The buffer may to some extent be microencapsulated or otherwise coated as granules with polymers and/or lipids being less soluble in saliva than is the one or more buffering agents. Such microencapsulation controls the dissolution rate whereby is extended the time frame of the buffering effect. In order to increase the buffering capacity still further without correspondingly increasing the pH, one may in specific embodiments use a second or auxiliary buffering agent to the first buffering agent, such as e g sodium or potassium bicarbonate buffers.

However, in a presently preferred embodiment an alkaline buffer is preferred, such as sodium carbonate.

In a presently preferred embodiment, the first buffer is sodium carbonate and the second buffer is sodium carbonate and sodium bicarbonate.

In a presently preferred embodiment the amount of the first buffer is 3 to 7.5 percent by weight of the gum base matrix and the buffer is sodium carbonate, and the amount of the second buffer is 1 to 3 percent by weight of the chewing gum composition and the buffer is sodium carbonate, and the amount of the second buffer is 0.5 to 1.5 percent by weight of the chewing gum composition and the buffer is sodium bicarbonate.

It is contemplated that the use of a first buffer in the gum base matrix and a second buffer in the chewing gum formulation, not added during the manufacture of the gum base matrix, gives a synergy in the sense that the pH profile is optimised. By adding buffer in a chewing gum formulation without adding buffer to the gum base matrix gives rise to an initial high pH peak which is a drawback for the consumer of the product since it gives a taste of the for instance a alkaline substance. This is avoided by adding both the first and the second buffer according to the invention.

According to the invention the presence of buffer allows in synergy with an active ingredient, such as an active pharmaceutical ingredient, to support the release. In particular when the active ingredient is dependent on pH, the buffer may support the release of the active ingredient so as to control the release of the active ingredient, such as an active pharmaceutical ingredient, such as nicotine.

In some embodiments of the invention, the gum base matrix comprises an environmentally degradable gum base polymer and optionally nicotine. In this embodiment nicotine is not necessary and thus the technical effect of the addition of cross-linked polyacrylic acid is provided in combination with the degradable polymer. It is contemplated that a cross-linked polyacrylic acid enhances the degradation of the degradable polymer by the binding of water in the chewing gum matrix during chewing.

In another aspect of the invention there is provided a method of producing a chewing composition with the cross-linked polyacrylic acid according to the invention providing a gum base matrix and a bulk portion, and adding a cross-linked polyacrylic acid as part of the bulk portion after mixing the gum base matrix.

In another aspect of the invention there is provided a method of enhancing the release of nicotine in a chewing gum comprising the chewing gum composition according to the invention.

In another aspect of the invention there is provided a method of enhancing the release of active ingredients in a chewing gum comprising a cross-linked polyacrylic acid according to the invention. In this aspect of the invention it is not necessary that nicotine is part of the chewing gum formulation. Other active ingredients may be used as alternatives for nicotine. It is believed that various active ingredients may be used and that the release of these active ingredients is enhanced as well. Thus, according to some embodiments of the invention the chewing gum formulation comprises at least one active ingredient.

The gum base matrix according to the present invention may comprise two or more ingredients selected from the group consisting of elastomers, elastomer plasticizers, resins, polyvinyl acetate, hydrogenated resins, polyterpene, fillers, fats and waxes, or any combination thereof.

It should be noted that various concentrations of gum base matrix in the final chewing gum core may be applied within the scope of the invention.

According to the invention a preferred amount of gum base matrix in the final chewing gum is above 30 percent by weight of the chewing gum core, such as above 35 percent by weight of the chewing gum core, such as above 40 percent by weight of the chewing gum core, such as above 45 percent by weight of the chewing gum core, such as about 40 percent by weight of the chewing gum core, such as about 47 percent by weight of the chewing gum core.

The composition of gum base formulations can vary substantially depending on the particular product to be prepared and on the desired masticatory and other sensory characteristics of the final product. However, typical ranges (% by weight) of the above gum base components are: 5 to 80% by weight elastomeric compounds, 5 to 80% by weight elastomer plasticizers, 0 to 40% by weight of waxes, 5 to 35% by weight softener, 0 to 50% by weight filler, and 0 to 5% by weight of miscellaneous ingredients such as antioxidants, colourants, etc. The gum base may comprise about 5 to about 95 percent, by weight, of the chewing gum, more commonly the gum base comprises 10 to about 60 percent, by weight, of the gum.

Elastomers provide the rubbery, cohesive nature to the gum, which varies depending on this ingredient's chemical structure and how it may be compounded with other ingredients. Elastomers suitable for use in the gum base and gum of the present invention may include natural or synthetic types.

Elastomer plasticizers vary the firmness of the gum base. Their specificity on elastomer inter-molecular chain breaking (plasticizing) along with their varying softening points cause varying degrees of finished gum firmness and compatibility when used in base. This may be important when one wants to provide more elastomeric chain exposure to the alkane chains of the waxes.

The elastomer compounds may be of natural origin but are preferably of synthetic origin, preferably synthetic polyesters.

The elastomers (rubbers) employed in the gum base may vary depending upon various factors such as the type of gum base desired, the texture of gum composition desired and the other components used in the composition to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base compositions include, without limitation, natural substances (of vegetable origin) such as chicle gum, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

According to the invention, the preferred molecular weight of the elastomers is below 500.000 (MW) to give a homogeneous product which is easier to manufacture and which provides an optimized release profile of pH, and/or active ingredients.

Natural resins may be used according to the invention and may be natural rosin esters, often referred to as ester gums including as examples glycerol esters of partially hydrogenated rosins, glycerol esters of polymerised rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the resin comprises terpene resins, e.g. derived from alpha-pinene, beta-pinene, and/or d-limonene, natural terpene resins, glycerol esters of gum rosins, tall oil rosins, wood rosins or other derivatives thereof such as glycerol esters of partially hydrogenated rosins, glycerol esters of polymerized rosins, glycerol esters of partially dimerised rosins, pentaerythritol esters of partially hydrogenated rosins, methyl esters of rosins, partially hydrogenated methyl esters of rosins or pentaerythritol esters of rosins and combinations thereof.

However, in a preferred embodiment of the invention polyterpene resins may be avoided in order to give a homogeneous product which is easier to manufacture and which provides an optimized release profile of pH, and/or active ingredients.

Gum bases are typically prepared by adding an amount of the elastomer, elastomer plasticizer and filler, and on occasion a vinyl polymer, to a heated (10° C.-120° C.) sigma blade mixer with a front to rear speed ratio of from about 1.2:1 to about 2:1, the higher ratio typically being used for gum base which requires more rigorous compounding of its elastomers.

The initial amounts of ingredients comprising the initial mass may be determined by the working capacity of the mixing kettle in order to attain a proper consistency and by the degree of compounding desired to break down the elastomer and increase chain branching. The higher the level of filler at the start or selection of a filler having a certain particle size distribution, the higher the degree of compounding and thus more of the elastomeric chain crosslinking are broken, causing more branching of the elastomer thus lower viscosity gum bases and thus softer final gum base and gum made from such a gum base. The longer the time of compounding, the use of lower molecular weight or softening point gum base ingredients, the lower the viscosity and firmness of the final gum base.

Compounding typically begins to be effective once the ingredients have massed together. Anywhere from 15 minutes to 90 minutes may be the length of compounding time.

Preferably, the time of compounding is from 20 minutes to about 60 minutes. The amount of added elastomer plasticizer depends on the level of elastomer and filler present. If too much elastomer plasticizer is added, the initial mass becomes over plasticized and not homogeneous.

After the initial ingredients have massed homogeneously and compounded for the time desired, the balance of the gum base ingredients are added in a sequential manner until a completely homogeneous molten mass is attained. Typically, any remainder of elastomer, elastomer plasticizer, vinyl polymer and filler, are added within 60 minutes after the initial compounding time. The filler and the elastomer plasticizer would typically be individually weighed and added in portions during this time. The optional waxes and the softeners are typically added after the elastomer and elastomer plasticizers and during the next 60 minutes. Then the mass is allowed to become homogeneous before dumping.

Typical gum base processing times may vary from about one to about three hours, preferably from about 1½ to 2½ hours, depending on the formulation. The final mass temperature when dumped may be between 70° C. and 130° C. and preferably between 100° C. and 120° C. The completed molten mass is emptied from the mixing kettle into coated or lined pans, extruded or cast into any desirable shape and allowed to cool and solidify. Those skilled in the art will recognize that many variations of the above-described procedure may be followed.

Chewing gum is prepared by mixing, rolling and scoring and may be done by a conventional procedure. Double sigma blade mixers are used for mixing the gum base with the other components of the formulation. The gum base may be softened in the mixer. By heat (from the heating jacket) and mixing, the gum base becomes plastic. So, the softened base is mixed with the liquid components, e.g. flavours, liquid, sorbitol and glycerol, optionally an active ingredient, such as nicotine in base form, and the solid materials, optionally active ingredients, such as nicotine in any form other than in liquid form, buffer, bulk sweetener, color as a powder mixture. The warm mass is discharged from the mixer in form of loaves stacked on trays on a truck and stored in a conditioned area until the next step starts. This is to cool the gum. After this, the rolling and scoring takes place. The gum is extruded into a thick sheet, which is rolled by multiple sets of calender rolls to the correct thickness. The scoring rolls, usually two sets, cut the gum into the correct size. The sheets are then transferred to a conditioned area on trays, where the sheets are cooled to make them brittle enough to be broken. The conditioned gum sheets are then passed through a breaker, which is a rotating drum that parts the sheets into separate pieces of gum along the scores.

In an embodiment of the invention, said chewing gum formulation comprises said gum base matrix and one or more chewing gum ingredients.

In an embodiment of the invention, said chewing gum ingredients are selected from the group consisting of bulk sweeteners, flavors, dry-binders, tabletting aids, anti-caking agents, emulsifiers, antioxidants, enhancers, absorption enhancers, buffers, high intensity sweeteners, softeners, colors, or any combination thereof.

In addition to the above water-insoluble gum base components, the bulk portion comprises a generally water-soluble part comprising a range of chewing gum additives. In the present context, the term "chewing gum additive" is used to designate any component, which in a conventional chewing gum manufacturing process is added to the gum base. The major proportion of such conventionally used additives is water soluble, but water-insoluble components, such as e.g. water-insoluble flavoring compounds, can also be included.

In the present context, chewing gum additives include bulk sweeteners, high intensity sweeteners, flavoring agents, softeners, emulsifiers, coloring agents, binding agents, acidulants, fillers, antioxidants and other components such as pharmaceutically or biologically active substances, conferring desired properties to the finished chewing gum product.

Suitable bulk sweeteners include both sugar and non-sugar sweetening components. Bulk sweeteners typically constitute from about 5 to about 95% by weight of the chewing gum, more typically about 20 to about 80% by weight such as 30 to 70% or 30 to 60% by weight of the gum.

Useful sugar sweeteners are saccharide-containing components commonly known in the chewing gum art including, but not limited to, sucrose, dextrose, maltose, dextrins, trehalose, D-tagatose, dried invert sugar, fructose, levulose, galactose, corn syrup solids, and the like, alone or in combination.

Sorbitol can be used as a non-sugar sweetener. Other useful non-sugar sweeteners include, but are not limited to, other sugar alcohols such as mannitol, xylitol, hydrogenated starch hydrolysates, maltitol, isomalt, erythritol, lactitol and the like, alone or in combination.

High intensity artificial sweetening agents can also be used alone or in combination with the above sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, sterioside and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another chewing gum component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners can be used in the chewing gum formulation processed in accordance with the invention. Additionally, the softener may also provide additional sweetness such as with aqueous sugar or alditol solutions.

In an embodiment of the invention, the chewing gum formulation comprise one or more chewing gum ingredients selected from the group consisting of bulk sweeteners, flavors, dry-binders, tabletting aids, anti-caking agents, emulsifiers, antioxidants, enhancers, absorption enhancers, buffers, or any combination thereof.

Further useful chewing gum base components include antioxidants, e.g. butylated hydroxytoluene (BHT), butyl hydroxyanisol (BHA), propylgallate and tocopherols, and preservatives.

A gum base formulation may, in accordance with the present invention, comprise one or more softening agents e.g. sucrose esters including those disclosed in WO 00/25598, which is incorporated herein by reference, tallow, hydrogenated tallow, hydrogenated and partially hydrogenated vegetable oils, cocoa butter, degreased cocoa powder, glycerol monostearate, glyceryl triacetate, lecithin, mono-, di- and triglycerides, acetylated monoglycerides, lanolin, sodium stearate, potassium stearate, glyceryl lecithin, propylene glycol monostearate, glycerine, fatty acids (e.g. stearic, palmitic, oleic and linoleic acids) and combinations thereof. As used herein the term "softener" designates an ingredient, which softens the gum base or chewing gum formulation and encompasses waxes, fats, oils, emulsifiers, surfactants and solubilisers.

To soften the gum base further and to provide it with water-binding properties, which confer to the gum base a pleasant smooth surface and reduce its adhesive properties, one or more emulsifiers is/are usually added to the composition, typically in an amount of 0 to 18% by weight, preferably 0 to 12% by weight of the gum base. Useful emulsifiers can include, but are not limited to, glyceryl monostearate, propylene glycol monostearate, mono- and diglycerides of edible fatty acids, lactic acid esters and acetic acid esters of mono- and diglycerides of edible fatty acids, acetylated mono and diglycerides, sugar esters of edible fatty acids, Na—, K—, Mg—and Ca-stearates, lecithin, hydroxylated lecithin and the like and mixtures thereof are examples of conventionally used emulsifiers which can be added to the chewing gum base. In case of the presence of a biologically or pharmaceutically active ingredient as defined below, the formulation may comprise certain specific emulsifiers and/or solubilisers in order to disperse and release the active ingredient.

Waxes and fats are conventionally used for the adjustment of the texture and for softening of the chewing gum base when preparing chewing gum bases. In connection with the present invention, any conventionally used and suitable type of natural and synthetic wax and fat may be used, such as for instance rice bran wax, polyethylene wax, petroleum wax (refined paraffin and microcrystalline wax), sorbitan monostearate, tallow, propylene glycol, paraffin, beeswax, carnauba wax, candelilla wax, cocoa butter, degreased cocoa powder and any suitable oil or fat, as e.g. completely or partially hydrogenated vegetable oils or completely or partially hydrogenated animal fats.

A chewing gum base formulation may, if desired, include one or more fillers/texturisers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, and combinations thereof.

In an embodiment of the invention, said chewing gum composition comprises a degradable gum base polymer.

In the present context, the term "degradable gum base polymer" refer to chewing gum base components which, after dumping the chewing gum, are capable of undergoing a physical, chemical and/or biological degradation whereby the dumped chewing gum waste becomes more readily removable from the site of dumping or is eventually disintegrated to lumps or particles which are no longer recognizable as being chewing gum remnants. The degradation or disintegration of such degradable polymers can be effected or induced by physical factors such as temperature, light, moisture, by chemical factors such as hydrolysis caused by a change in pH or by the action of enzymes capable of degrading the polymers. In other useful embodiments all of the polymer components of the gum base are environmentally degradable or biodegradable polymers.

Preferably, the ultimate degradation products are carbon dioxide, methane and water.

According to a preferred definition of biodegradability according to the invention, biodegradability is a property of certain organic molecules whereby, when exposed to the natural environment or placed within a living organism, they react through an enzymatic or microbial process, often in combination with a pure chemical process such as hydrolysis, to form simpler compounds, and ultimately, carbon dioxide, nitrogen oxides, methane and water.

An important feature of the degradable polymers as used herein is that they contain chemical unstable bonds that can be broken in the chewed chewing gum under environmental conditions. In the present context, the term "environmental condition" denotes indoor and outdoor locations and the temperature, light and humidity conditions prevailing in such environments. It will be appreciated that the rate of degradation of the degradable polymer in chewing gum remnants dropped in a given environment will depend on the above physical conditions. In preferred embodiments, the degradable polymer is one where, under any given environmental conditions except extreme cold temperature conditions, i.e. at temperatures below 0° C., at least 5% of unstable bonds, preferably at least 10%, more preferably at least 15% including at least 25% of unstable bonds are broken after one month to 12 months under environmental conditions.

Accordingly, suitable examples of additional environmentally or biologically degradable chewing gum base polymers, which can be applied in accordance with the gum base of the present invention, include degradable polyesters, poly(ester-carbonates), polycarbonates, polyester amides, polypeptides, homopolymers of amino acids such as polylysine, and proteins including derivatives thereof such as e.g. protein hydrolysates including a zein hydrolysate. Particularly useful compounds of this type include polyester polymers obtained by the polymerisation of one or more cyclic esters such as lactide, glycolide, trimethylene carbonate, δ-valerolactone, β-propiolactone and ε-caprolactone, and polyesters obtained by polycondensation of a mixture of open-chain polyacids and polyols, for example, adipic acid and di(ethylene glycol). Hydroxy carboxylic acids such as 6-hydroxycaproic acid may also be used to form polyesters or they may be used in conjunction with mixtures of polyacids and polyols. Such degradable polymers may be homopolymers, copolymers or terpolymers, including graft- and block-polymers.

In an embodiment of the invention, the chewing gum core is provided with an outer coating.

In an embodiment of the invention, said outer coating is selected from the group consisting of hard coating, soft coating and edible film-coating or any combination thereof.

In some other embodiments of the invention the active ingredient is selected from the group consisting of phytochemicals, such as resveratrol and anthocyanine; herbals, such as green tea or thyme; antioxidants, such as polyphenols; micronutrients; mouth moisteners, such as acids; throat soothing ingredients; appetite suppressors; breath fresheners, such as zinc compounds or copper compounds; diet supplements; cold suppressors; cough suppressors; vitamins, such as vitamin A, vitamin C or vitamin E; minerals, such as chromium; metal ions; alkaline materials, such as carbonates; salts; herbals, dental care agents, such as remineralisation agents, antibacterial agents, anti-caries agents, plaque acid buffering agents, tooth whiteners, stain removers or desensitizing agents; and combinations thereof.

According to the invention the active ingredient may be selected from the group consisting of antihistamines, anti-smoking agents, agents used for diabetes, decongestants, peptides, pain-relieving agents, nausea-relieving agents, statines, or any combination thereof.

In an embodiment of the invention, wherein the pharmaceutically active ingredients are selected from the group consisting of cetirizine, levo cetirizine, nicotine, nicotine polacrilex, nicotine in combination with alkaline agents, metformine, metformine HCL, phenylephrine, GLP-1, exenatide, deca-peptide, KSL-W (acetat), fluor, chlorhexidine, or any combination thereof.

In an embodiment of the invention, the pharmaceutically active ingredients are selected from the group consisting of loratadine, des-loratadine, nicotine bitartrate, nicotine in combination with caffeine, nicotine antagonists, combinations thereof or compounds comprising one or more of these, pseudoephedrine, flurbiprofen, paracetamol, acetylsalicylic acid, Ibuprofen, antacida, cimetidine, ranitidine, ondansetron, granisetron, metoclopramid, simvastatin, lovastatin, fluvastatin, acyclovir, benzydamin, rimonabant, varenicline, sildenafil, naltrexone, fluor in combination with fruit acids, derivatives, salts or isomers of chlorhexidine, or any combination thereof.

In an embodiment of the invention, the chewing gum formulation comprises a pharmaceutically active ingredient in the form of nicotine polacrilex resin and the buffer in the form of sodium bicarbonate and sodium carbonate.

In an embodiment of the invention, at least a part of the pharmaceutically active ingredients are adhered to dry-binder particles.

In an embodiment of the invention, at least a part of said active ingredients are incorporated in the chewing gum core.

In an embodiment of the invention, said active ingredient is selected from the group consisting of anti-histamines, decongestants, smoking cessation aids, diabetes II agents, or any combination thereof.

In an embodiment of the invention, said active ingredient is selected from the group consisting of metformin, cetirizine, levo cetirizine, phenylephrine, flurbiprofen, nicotine, nicotine bitartrate, nicotine polacrilex, nicotine in combination with alkaline agents, nicotine in combination with caffeine, sodium picosulfate, fluor, fluor in combination with fruit acids, chlorhexidine, or any derivatives thereof, salts thereof, isomers thereof, nicotine antagonists, combinations thereof or compounds comprising one or more of these.

In an embodiment of the invention, said active ingredient is selected from the group consisting of ephedrine, pseudo ephedrine, caffeine, loratadine, sildenafil, simvastatin, sumatriptan, acetaminophen, calcium carbonate, vitamin D, ibuprofen, aspirin, alginic acid in combination with aluminum hydroxide and sodium bicarbonate, ondansetron, Tibolon, Rimonabant, Varenicline, allergenes, sitagliptin or any derivatives thereof, salts thereof, isomers thereof, combinations thereof or compounds comprising one or more of these.

In some embodiments, a delivery system may be included. In some embodiments, the ingredients may be encapsulated or otherwise included separately in different delivery systems. Alternatively, in some embodiments the ingredients may be encapsulated or otherwise included in the same delivery system. As another possibility, one or more of the ingredients may be free (e.g. unencapsulated) while one or more other ingredients may be encapsulated. A chewing gum according to the invention may include a group of ingredients for which managed release of the group during consumption of the chewing gum formulation is desired. Groups of two or more ingredients for which managed release from a chewing gum during consumption of the chewing gum may be desired include, but are not limited to: color and flavor, multiple flavors, multiple colors, cooling agent and flavor, warming agent and flavor, cooling agent and warming agent, cooling agent and high-intensity sweetener, warming agent and high-intensity sweetener, multiple cooling agents (e.g., WS-3 and WS-23, WS-3 and menthyl succinate), menthol and one or more cooling agents, menthol and one or more warming agents, multiple warming agents, high-intensity sweetener(s) and tooth whitening active(s), high-intensity sweetener(s) and breath-freshening active(s), an ingredient with some bitterness and a bitterness suppressor for the ingredient, multiple high-intensity sweeteners (e.g., acesulfame-k and aspartame), multiple tooth whitening active ingredients (e.g., an abrasive ingredient and an antimicrobial ingredient, a peroxide and a nitrate, a warming agent and a polyol, a cooling agent and a polyol, multiple polyols, a warming agent and micronutrient, a cooling agent and a micronutrient, a warming agent and a mouth moistening agent, a cooling agent and a mouth moistening agent, a warming agent and a throat care agent, a cooling agent and a throat care agent, a warming agent and a food acid, a cooling agent and food acid, a warming agent and an emulsifier/surfactant, a cooling agent and an emulsifier/surfactant, a warming agent and a color, a cooling agent and a color, a warming agent and a flavor potentiator, a cooling agent and a flavor potentiator, a warming agent with sweetness potentiator, a cooling agent with a sweetness potentiator, a warming agent and an appetite suppressant, a cooling agent and an appetite suppressant, a high-intensity sweetener and a flavor, a cooling agent and a teeth-whitening agent, a warming agent and a teeth-whitening agent, a warming agent and breath-freshening agent, a cooling agent and a breath-freshening agent, a cooling agent and an effervescing system, a warming agent and an effervescing system, a warming agent and an antimicrobial agent, a cooling agent and an antimicrobial agent, multiple anticalcums ingredients, multiple remineralization ingredients, multiple surfactants, remineralization ingredients with demineralization ingredients, acidic ingredients with acid buffering ingredients, anticalculus ingredients with antibacterial ingredients, remineralization ingredients with anticalculus ingredients, anticalculus ingredients with remineralization ingredients with antibacterial ingredients, surfactant ingredients with anticalculus ingredients, surfactant ingredients with antibacterial ingredients, surfactant ingredients with remineralization ingredients, surfactants with anticalculus ingredients with antibacterial ingredients, multiple types of vitamins or minerals, multiple micronutrients, multiple acids, multiple antimicrobial ingredients, multiple breath-freshening ingredients, breath-freshening ingredients and antimicrobial ingredients, multiple appetite suppressors, acids and bases that react to effervesce, a bitter compound with a high-intensity sweetener, a cooling agent and an appetite suppressant, a warming agent and an appetite suppressant, a high-intensity sweetener and an appetite suppressant, a high-intensity sweetener with an acid, a probiotic ingredient and a prebiotic ingredient, a vitamin and a mineral, a metabolic enhancement ingredient with a macronutrient, a metabolic enhancement ingredient with a micronutrient, an enzyme with a substrate, a high-intensity sweetener with a sweetness potentiator, a cooling compound with a cooling potentiator, a flavor with a flavor potentiator, a warming compound with a warming potentiator, a flavor with salt, a high-intensity sweetener with salt, an acid with salt, a cooling compound with salt, a warming compound with salt, a flavor with a surfactant, an astringent compound with an ingredient to provide a sensation of hydration, etc. In some embodiments, the multiple ingredients may be part of the same delivery system or may be part of different delivery systems. Different delivery systems may use the same or different encapsulating materials.

In some embodiments, antitussive ingredients such as chlophedianol hydrochloride, codeine, codeine phosphate, codeine sulfate, dextromethorphan, dextromethorphan hydrobromide, diphenhydramine citrate, and diphenhydramine hydrochloride, and combinations thereof can be included.

In some embodiments, throat soothing agents such as honey, propolis, aloe vera, glycerine, menthol and combinations thereof can be included. In still other embodiments, cough suppressants can be included. Such cough suppressants can fall into two groups: those that alter the texture or production of phlegm such as mucolytics and expectorants; and those that suppress the coughing reflex such as codeine (narcotic cough suppressants), antihistamines, dextromethorphan and isoproterenol (non-narcotic cough suppressants). In some embodiments, ingredients from either or both groups can be included.

In still other embodiments, antitussives can include, but are not limited to, the group consisting of codeine, dextromethorphan, dextrorphan, diphenhydramine, hydrocodone, noscapine, oxycodone, pentoxyverine and combinations thereof. In some embodiments, antihistamines can include, but are not limited to, acrivastine, azatadine, brompheniramine, chlo[phi]heniramine, clemastine, cyproheptadine, dexbrompheniramine, dimenhydrinate, diphenhydramine, doxylamine, hydroxyzine, meclizine, phenindamine, phenyltoloxamine, promethazine, pyrilamine, tripelennamine, triprolidine and combinations thereof. In some embodiments, non-sedating antihistamines can include, but are not limited to, astemizole, cetirizine, ebastine, fexofenadine, loratidine, terfenadine, and combinations thereof.

In some embodiments, expectorants can include, but are not limited to, ammonium chloride, guaifenesin, ipecac fluid extract, potassium iodide and combinations thereof. In some embodiments, mucolytics can include, but are not limited to, acetylcycsteine, ambroxol, bromhexine and combinations thereof. In some embodiments, analgesic, antipyretic and anti-inflammatory agents can include, but are not limited to, acetaminophen, aspirin, diclofenac, diflunisal, etodolac, fenoprofen, flurbiprofen, ibuprofen, ketoprofen, ketorolac, nabumetone, naproxen, piroxicam, caffeine and mixtures thereof. In some embodiments, local anesthetics can include, but are not limited to, lidocaine, benzocaine, phenol, dyclonine, benzonotate and mixtures thereof. In some embodiments nasal decongestants and ingredients that provide the perception of nasal clearing can be included. In some embodiments, nasal decongestants can include but are not limited to phenylpropanolamine, pseudoephedrine, ephedrine, phenylephrine, oxymetazoline, and combinations thereof. In some embodiments ingredients that provide a perception of nasal clearing can include but are not limited to menthol, camphor, borneol, ephedrine, eucalyptus oil, peppermint oil, methyl salicylate, bornyl acetate, lavender oil, wasabi extracts, horseradish extracts, and combinations thereof. In some embodiments, a perception of nasal clearing can be provided by odoriferous essential oils, extracts from woods, gums, flowers and other botanicals, resins, animal secretions, and synthetic aromatic materials.

Typically, encapsulation of a throat care agent will result in a delay in the release of the predominant amount of the active ingredient during consumption of a chewing gum that includes the encapsulated throat care agent (e.g. as part of a delivery system added as an ingredient to the chewing gum). In some embodiments, the release profile of the ingredient (e.g. the dental care active ingredient) can be managed for a gum by managing various characteristics of the ingredient, delivery system containing the ingredient, and/or the chewing gum containing the delivery system and/or how the delivery system is made. For example, characteristics might include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In an embodiment of the invention, said active ingredient is selected from the group consisting of phytochemicals, such as resveratrol and anthocyanine; herbals, such as green tea or thyme; antioxidants, such as polyphenols; micronutrients; mouth moisteners, such as acids; throat soothing ingredients; appetite suppressors; breath fresheners, such as zinc compounds or copper compounds; diet supplements; cold suppressors; cough suppressors; vitamins, such as vitamin A, vitamin C or vitamin E; minerals, such as chromium; metal ions; alkaline materials, such as carbonates; salts; herbals, dental care agents, such as remineralisation agents, antibacterial agents, anti-caries agents, plaque acid buffering agents, tooth whiteners, stain removers or desensitizing agents; and combinations thereof.

In addition to essential oils and chemicals derived from them, in some embodiments, breath fresheners can include but are not limited to zinc citrate, zinc acetate, zinc fluoride, zinc ammonium sulfate, zinc bromide, zinc iodide, zinc chloride, zinc nitrate, zinc fluorosilicate, zinc gluconate, zinc tartarate, zinc succinate, zinc formate, zinc chromate, zinc phenol sulfonate, zinc dithionate, zinc sulfate, silver nitrate, zinc salicylate, zinc glycerophosphate, copper nitrate, chlorophyll, copper chlorophyll, chlorophyllin, hydrogenated cottonseed oil, chlorine dioxide, beta cyclodextrin, zeolite, silica-based materials, carbon-based materials, enzymes such as laccase, and combinations thereof. In some embodiments, the release profiles of probiotics can be managed for a gum including, but not limited to lactic acid producing microorganisms such as *Bacillus coagulans, Bacillus subtilis, Bacillus laterosporus, Bacillus laevolacticus, Sporolactobacillus inulinus, Lactobacillus acidophilus, Lactobacillus curvatus, Lactobacillus plantarum, Lactobacillus jenseni, Lactobacillus casei, Lactobacillus fermentum, Lactococcus lactis, Pedioccocus acidilacti, Pedioccocus pentosaceus, Pedioccocus urinae, Leuconostoc mesenteroides, Bacillus coagulans, Bacillus subtilis, Bacillus laterosporus, Bacillus laevolacticus, Sporolactobacillus inulinus* and mixtures thereof. Breath fresheners are also known by the following trade names: Retsyn™, Actizol™, and Nutrazin™. Examples of malodor-controlling compositions are also included in U.S. Pat. No. 5,300,305 to Stapler et al. and in U.S. Patent Application Publication Nos. 2003/0215417 and 2004/0081713 which are incorporated in their entirety herein by reference for all purposes.

Typically, encapsulation of the breath-freshening ingredient will result in a delay in the release of the predominant amount of the active ingredient during consumption of a chewing gum that includes the encapsulated breath-freshening ingredient (e.g., as part of a delivery system added as an ingredient to the chewing gum composition). In some embodiments, the release profile of the ingredient (e.g., the breath-freshening ingredient) can be managed for a gum by managing various characteristics of the ingredient, delivery system containing the ingredient, and/or the chewing gum containing the delivery system and/or how the delivery system is made. For example, characteristics might include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the chewing gum, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

In some embodiments, minerals can include but are not limited to sodium, magnesium, chromium, iodine, iron, manganese, calcium, copper, fluoride, potassium, phosphorous, molybdenum, selenium, zinc, and combinations thereof.

In some embodiments micronutrients can include but are not limited to L-carnitine, choline, coenzyme Q10, alpha-lipoic acid, omega-3-fatty acids, pepsin, phytase, trypsin, lipases, proteases, cellulases, and combinations thereof.

Antioxidants can include materials that scavenge free radicals. In some embodiments, antioxidants can include but are not limited to ascorbic acid, citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

In some embodiments, phytochemicals can include but are not limited to cartotenoids, chlorophyll, chlorophyllin, fiber, flavanoids, anthocyanins, cyaniding, delphinidin, malvidin, pelargonidin, peonidin, petunidin, flavanols, catechin, epicatechin, epigallocatechin, epigallocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof.

In some embodiments dental care ingredients may be included (also known as oral care ingredients) and may be tooth whiteners, stain removers, oral cleaning, bleaching agents, desensitizing agents, dental remineralization agents, antibacterial agents, anticaries agents, plaque acid buffering agents, surfactants and anticalculus agents. Non-limiting examples of such ingredients can include, hydrolytic agents including proteolytic enzymes, abrasives such as hydrated silica, calcium carbonate, sodium bicarbonate and alumina, other active stain-removing components such as surface-active agents, including, but not limited to anionic surfactants such as sodium stearate, sodium palminate, sulfated butyl oleate, sodium oleate, salts of fumaric acid, glycerol, hydroxylated lecithin, sodium lauryl sulfate and chelators such as polyphosphates, which are typically employed as tartar control ingredients. In some embodiments, dental care ingredients can also include tetrasodium pyrophosphate and sodium tri-polyphosphate, sodium bicarbonate, sodium acid pyrophosphate, sodium tripolyphosphate, xylitol, sodium hexametaphosphate. In some embodiments, peroxides such as carbamide peroxide, calcium peroxide, magnesium peroxide, sodium peroxide, hydrogen peroxide, and peroxydiphospate are included. In some embodiments, potassium nitrate and potassium citrate are included. Other examples can include casein glycomacropeptide, calcium casein peptone-calcium phosphate, casein phosphopeptides, casein phosphopeptide-amorphous calcium phosphate (CPP-ACP), and amorphous calcium phosphate. Still other examples can include papaine, krillase, pepsin, trypsin, lysozyme, dextranase, mutanase, glycoamylase, amylase, glucose oxidase, and combinations thereof. Further examples can include surfactants such as sodium stearate, sodium ricinoleate, and sodium lauryl sulfate surfactants for use in some embodiments to achieve increased prophylactic action and to render the dental care ingredients more cosmetically acceptable. Surfactants can preferably be detersive materials which impart to the composition detersive and foaming properties. Suitable examples of surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine. In addition to surfactants, dental care ingredients can include antibacterial agents such as, but not limited to, triclosan, chlorhexidine, zinc citrate, silver nitrate, copper, limonene, and cetyl pyridinium chloride. In some embodiments, additional anticaries agents can include fluoride ions or fluorine-providing components such as inorganic fluoride salts. In some embodiments, soluble alkali metal salts, for example, sodium fluoride, potassium fluoride, sodium fluorosilicate, ammonium fluorosilicate, sodium monofluorophosphate, as well as tin fluorides, such as stannous fluoride and stannous chloride can be included. In some embodiments, a fluorine-containing compound having a beneficial effect on the care and hygiene of the oral cavity, e.g., diminution of enamel solubility in acid and protection of the teeth against decay may also be included as an ingredient. Examples thereof include sodium fluoride, stannous fluoride, potassium fluoride, potassium stannous fluoride ($SnF_2$-KF), sodium hexafluorostannate, stannous chlorofluoride, sodium fluorozirconate, and sodium monofluorophosphate. In some embodiments, urea is included. Further examples are included in the following U.S. patents and U.S. published patent applications, the contents of all of which are incorporated in their entirety herein by reference for all purposes: U.S. Pat. No. 5,227,154 to Reynolds, U.S. Pat. No. 5,378,131 to Greenberg, U.S. Pat. No. 6,846,500 to Luo et al, U.S. Pat. No. 6,733,818 to Luo et al., U.S. Pat. No. 6,696,044 to Luo et al., U.S. Pat. No. 6,685,916 to Holme et al., U.S. Pat. No. 6,485,739 to Luo et al., U.S. Pat. No. U.S. Pat. No. 6,479,071 to Holme et al., U.S. Pat. No. 6,471,945 to Luo et al., U.S. Patent Publication Nos. 20050025721. to Holme et al., 2005008732 to Gebreselassie et al., and 20040136928 to Holme et al.

In an embodiment of the invention, said active ingredient is selected from the group consisting of di-peptides, tri-peptides, oligo-peptides, deca-peptides, deca-peptide KSL, deca-peptide KSL-W, amino acids, proteins, or any combination thereof.

In an embodiment of the invention, said active ingredient comprises a probiotic bacteria, such as lactobacilli, bifidobacteria, *lactococcus, streptococcus, leuconostoccus, pediococcus* or *enterococcus*.

In an embodiment of the invention, said active ingredient comprises a prebiotic, such as fructose, galactose, mannose, insulin or soy.

The following list discloses examples of active ingredients which can be classified according to the ATC classification mentioned above and which are active ingredients which may be used according to the invention: Ephedrine, Magaldrate, Pseudoephedrine, Sildenafil, Xylocaine, Benzalconium chloride, Caffeine, Phenylephrine, Amfepramone, Orlistat, Sibutramine, Acetaminophen, Aspirin, Aluminum amino acetate, Aluminum amino acetate in combination with Magnesium oxide, Aluminum oxide hydrate in combination with Magnesiumoxide, Calcium carbonate in combination with Magnesium hydroxide, Calciumcarbonate, Dihydroxy Aluminum sodium carbonate, Magnesiumoxide, Glitazones, Metformin, Chlorpromazine, Dimenhydrinat, Domperidone, Meclozine, Metoclopramide, Odansetron, Prednisolone, Promethazine, Acrivastine, Cetirizine, Cinnarizine, Clemastine, Cyclizine, Desloratadine, Dexchlorpheniramine, Dimenhydrinate, Ebastine, Fexofenadine, Ibuprofen, Levolevoproricin, Loratadine, Meclozine, Mizolastine, Promethazine, Miconazole, Vitamin B12, Folic acid, Ferro compounds, vitamin C, Chlorhexidine diacetate, Fluoride, Decapeptide KSL, Aluminum fluoride, Aminochelated calcium, Ammonium fluoride, Ammonium fluorosilicate, Ammonium monofluorphosphate, Calcium fluoride, Calcium gluconate, Calcium glycerophosphate, Calcium lactate, Calcium monofluorphosphate, Calciumcarbonate, Carbamide, Cetyl pyridinium chloride, Chlorhexidine, Chlorhexidine digluconate, Chlorhexidine Chloride, Chlorhexidine diacetate, CPP Caseine Phospho Peptide, Hexetedine, Octadecentyl Ammonium fluoride, Potasium fluorosilicate, Potassium Chloride, Potassium monofluorphosphate, Sodium bi carbonate, Sodium carbonate, Sodium fluoride, Sodium fluorosilicate, Sodium monofluorphosphate, Sodium tri polyphosphate, Stannous fluoride, Stearyl Trihydroxyethyl Propylenediamine Dihydrofluoride, Strontium chloride, Tetra potassium pyrophosphate, Tetra sodium pyrophosphate, Tripotassium orthophosphate, Trisodium orthophosphate, Alginic acid, Aluminum hydroxide, Sodium bicarbonate, Sildenafil, Tadalafil, Vardenafil, Yohimbine, Cimetidine, Nizatidine, Ranitidine, Acetylsalicylic acid, Clopidogrel, Acetylcysteine, Bromhexine, Codeine, Dextromethorphan, Diphenhydramine, Noscapine, Phenylpropanolamine, vitamin D, Simvastatin, Bisacodyl, Lactitol, Lactulose, Magnesium oxide, Sodium picosulfate, Senna glycosides, Benzocaine, Lidocaine, Tetracaine, Almotriptan, Eletriptan, Naratriptan, Rizatriptan, Sumatriptan, Zolmitriptan, Calcium, Chromium, Copper, Iodine, Iron, Magnesium, Manganese, Molybdenium, Phosphor, Selenium, Zinc, Nicotine, Nicotine bitartrate, Nicotine pftalate, Nicotine polacrilex, Nicotine sulphate, Nicotine tartrate, Nicotine citrate, Nicotine lactate, Chloramine, Hydrogenperoxide, Metronidazole, Triamcinolonacetonide, Benzethonium Chl., Cetyl pyrid. Chl., Chlorhexidine, Fluoride, Lidocaine, Amphotericin, Miconazole, Nystatin, Fish oil, Ginkgo Biloba, Ginseng, Ginger, Purple coneflower, Saw Palmetto, Cetirizine, Levocetirizine, Loratadine, Diclofenac, Flurbiprofen, Acrivastine Pseudoephedrine, Loratadine Pseudoephedrine, Glucosamine, hyaluronic acid, Decapeptide KSL-W, Decapeptide KSL, Resveratrol, Misoprostol, Bupropion, Nicotine, Ondansetron HCl, Esomeprazole, Lansoprazole, Omeprazole, Pantoprazole, Rabeprazole, Bacteria and the like, Loperamide, Simethicone, Acetylsalicylic acid and others, Sucralfate, Vitamin A, Vitamin B1, Vitamin B12, Vitamin B2, Vitamin B6, Biotin, Vitamin C, Vitamin D, Vitamin E, Folinic acid, Vitamin K, Niacin, Q10, Clotrimazole, Fluconazole, Itraconazole, Ketoconazole, Terbinafine, Allopurinol, Probenecid, Atorvastatin, Fluvastatin, Lovastatin, Nicotinic acid, Pravastatin, Rosuvastatin, Simvastatin, Pilocarpine, Naproxen, Alendronate, Etidronate, Raloxifene, Risedronate, Benzodiazepines, Disulfuram, Naltrexone, Buprenorphine, Codeine, Dextropropoxyphene, Fentanyl, Hydromorphone, Ketobemidone, Ketoprofen, Methadone, Morphine, Naproxen, Nicomorphine, Oxycodone, Pethidine, Tramadol, Amoxicillin, Ampicillin, Azithromycin, Ciprofloxacin, Clarithromycin, Doxycyclin, Erythromycin, Fusidic acid, Lymecycline, Metronidazole, Moxifloxacin, Ofloxacin, Oxytetracycline, Phenoxymethylpenicillin, Rifamycins, Roxithromycin, Sulfamethizole, Tetracycline, Trimethoprim, Vancomycin, Acarbose, Glibenclamide, Gliclazide, Glimepiride, Glipizide, Insulin, Repaglinide, Tolbutamide, Oseltamivir, Aciclovir, Famciclovir, Penciclovir, Valganciclovir, Amlopidine, Diltiazem, Felodipine, Nifedipine, Verapamil, Finasteride, Minoxidil, Cocaine, Buphrenorphin, Clonidine, Methadone, Naltrexone, Calciumantagonists, Clonidine, Ergotamine, β-blockers, Aceclofenac, Celecoxib, Dexiprofen, Etodolac, Indometacin, Ketoprofen, Ketorolac, Lornoxicam, Meloxicam, Nabumetone, Oiroxicam, Parecoxib, Phenylbutazone, Piroxicam, Tiaprofenic acid, Tolfenamic acid, Aripiprazole, Chlorpromazine, Chlorprothixene, Clozapine, Flupentixol, Fluphenazine, Haloperidol, Lithium carbonate, Lithium citrate, Melperone, Penfluridol, Periciazine, Perphenazine, Pimozide, Pipamperone, Prochlorperazine, Risperidone, Thioridizin, Fluconazole, Itraconazole, Ketoconazole, Voriconazole, Opium, Benzodiazepines, Hydroxine, Meprobamate, Phenothiazine, Aluminiumaminoacetate, Esomeprazole, Famotidine, Magnesium oxide, Nizatide, Omeprazole, Pantoprazole, Fluconazole, Itraconazole, Ketoconazole, Metronidazole, Amphetamine, Atenolol, Bisoprolol fumarate, Metoprolol, Metropolol, Pindolol, Propranolol, Auranofin, and Bendazac.

Further examples of useful active ingredients include active ingredients selected from the therapeutical groups comprising: Analgesic, Anaestetic, Antipyretic, Anti allergic, Anti-arrytmic, Appetite suppressant, Antifungal, Anti-inflammatory, Broncho dilator, Cardiovascular drugs, Coronary dilator, Cerebral dilator, Peripheral vasodilator, Anti-infective, Psychotropic, Anti-manic, Stimulant, Antihistamine, Laxative, Decongestrant, Gastro-intestinal sedative, Sexual dysfunction agent, Desinfectants, Anti-diarrheal, Anti-anginal substance, Vasodilator, Anti-hypertensive agent, Vasoconstrictor, Migraine treating agent, Antibiotic, Tranquilizer, Ntipsychotic, Anti-tumor drug, Anticoagulant, Antithrombotic agent, Hypnotic, Sedative, Anti-emetic, Anti-, auseant, Anticonvulsant, Neuromuscular agent, Hyper and hypoglycaemic, Thyroid and antithyroid, Diuretic, Antispasmodic, Uterine relaxant, Anti-obesity agent, Anoretic, Spasnolytics, Anabolic agent, Erythropoietic agent, Anti-asthmatic, Expectorant, Cough suppressant, Mucolytic, Anti-uricemic agent, Dental vehicle, Breath freshener, Antacid, Anti-diuretc, Anti-flatulent, Betablocker, Teeth Whitener, Enzyme, Co-enzyme, Protein, Energy booster, Fiber, Probiotics, Prebiotics, Antimicrobial agent, NSAID, Anti-tussives, Decongestrants, Anti-histamines, Expectorants, Anti-diarrheals, Hydrogen antagonists, Proton pump inhibitors, General nonselective CNS depressants, General nonselective CNS stimulants, Selectively CNS function modyfying drugs, Antiparkinsonism, Narcotic-analgetics, Analgetic-antipyretics, Psychopharmacological drugs, and Sexual dysfunction agents.

Examples of useful active ingredients include: Casein glyco-macro-peptide (CGMP), Nicotine, Nicotine bitartrate, Nicotine sulphate, Nicotine tartrate, Nicotine pftalate, Nicotine lactate, Nicotinecitrate, Nicotine polacrilex, Triclosan, Cetyl pyridinium chloride, Domiphen bromide, Quarternary ammonium salts, Zinc components, Sanguinarine, Fluorides, Alexidine, Octonidine, EDTA, Aspirin, Acetaminophen, Ibuprofen, Ketoprofen, Diflunisal, Fenoprofen calcium, Naproxen, Tolmetin sodium, Indomethacin, Benzonatate, Caramiphen edisylate, Menthol, Dextromethorphan hydrobromide, Theobromine hydrochloride, Chlophendianol Hydrochloride, Pseudoephedrine Hydrochloride, Phenylephrine, Phenylpropanolamine, Pseudoephedrine sulphate, Brompheniramine maleate, Chlorpheniramine-maleate, Carbinoxamine maleate, Clemastine fumarate, Dexchlorpheniramine maleate, Dephenhydramine hydrochloride, Diphenpyralide hydrochloride, Azatadine maleate, Diphenhydramine citrate, Doxylamine succinate, Promethazine hydrochloride, Pyrilamine maleate, Tripellenamine citrate, Triprolidine hydrochloride, Acrivastine, Loratadine, Brompheniramine, Dexbrompheniamine, Guaifenesin, Ipecac, Potassium iodide, Terpin hydrate, Loperamide, Famotidine, Ranitidine, Omeprazole, Lansoprazole, Aliphatic alcohols, Barbiturates, Caffeine, Nicotine, Strychnine, Picrotoxin, Pentyenetetrazol, Phenyhydantoin, Phenobarbital, Primidone, Carbamazapine, Etoxsuximide, Methsuximide, Phensuximide, Trimethadione, Diazepam, Benzodiazepines, Phenacemide, Pheneturide, Acetazolamide, Sulthiame, Bromide, Levodopa, Amantadine, Morphine, Heroin, Hydromorphone, Metopon, Oxymorphone, Levophanol, Codeine, Hydrocodone, Xycodone, Nalorphine, Naloxone, Naltrexone, Salicylates, Phenylbutazone, Indomethacin, Phenacetin, Chlorpromazine, Methotrimeprazine, Haloperidol, Clozapine, Reserpine, Imipramine, Tranylcypromine, Phenelzine, Lithium, Sildenafil citrate, Tadalafil, and Vardenafil CL.

Examples of useful active ingredients include active ingredients selected from the groups of ace-inhibitors, anti-anginal drugs, anti-arrhythmias, anti-asthmatics, anti-cholesterolemics, analgesics, anesthetics, anticonvulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplasties, antiparkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra™, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocriptine or nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of active ingredients contemplated for use in the present invention can include antacids, H2-antagonists, and analgesics. For example, antacid dosages can be prepared using the ingredients calcium carbonate alone or in combination with magnesium hydroxide, and/or aluminum hydroxide. Moreover, antacids can be used in combination with H2-antagonists.

Analgesics include opiates and opiate derivatives, such as Oxycontin™, ibuprofen, aspirin, acetaminophen, and combinations thereof that may optionally include caffeine.

Other drug active ingredients for use in embodiments can include anti-diarrheals such as Immodium™ AD, anti-histamines, anti-tussives, decongestants, vitamins, and breath fresheners. Also contemplated for use herein are anxiolytics such as Xanax™; anti-psychotics such as Clozaril™ and Haldol™; non-steroidal anti-inflammatories (NSAID's) such as ibuprofen, naproxen sodium, Voltaren™ and Lodine™, anti-histamines such as Claritin™, Hismanal™, Relafen™, and Tavist™; antiemetics such as Kytril™ and Cesamet™; bronchodilators such as Bentolin™, Proventil™; anti-depressants such as Prozac™, Zoloft™, and Paxil™; anti-migraines such as Imigra™, ACE-inhibitors such as Vasotec™, Capoten™ and Zestril™; anti-Alzheimer's agents, such as Nicergoline™; and CaH-antagonists such as Procardia™, Adalat™, and Calan™.

The popular H2-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients can include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

A variety of nutritional supplements may also be used as active ingredients including virtually any vitamin or mineral. For example, vitamin A, vitamin C, vitamin D, vitamin E, vitamin K, vitamin B6, vitamin B12, thiamine, riboflavin, biotin, folic acid, niacin, pantothenic acid, sodium, potassium, calcium, magnesium, phosphorus, sulfur, chlorine, iron, copper, iodine, zinc, selenium, manganese, choline, chromium, molybdenum, fluorine, cobalt and combinations thereof, may be used. Examples of nutritional supplements that can be used as active ingredients are set forth in U.S. Patent Application Publication Nos. 2003/0157213 A1, 2003/0206993 and 2003/0099741 A1 which are incorporated in their entirety herein by reference for all purposes. Various herbals may also be used as active ingredients such as those with various medicinal or dietary supplement properties. Herbals are generally aromatic plants or plant parts and or extracts thereof that can be used medicinally or for flavoring. Suitable herbals can be used singly or in various mixtures. Commonly used herbs include Echinacea, Goldenseal, *Calendula*, Rosemary, Thyme, Kava, Aloe, Blood Root, Grapefruit Seed Extract, Black Cohosh, Ginseng, Guarana, Cranberry, Ginko Biloba, St. John's Wort, Evening Primrose Oil, Yohimbe Bark, Green Tea, Ma Huang, Maca, Bilberry, Lutein, and combinations thereof.

In an embodiment of the invention, said chewing gum formulation comprises one or more encapsulation delivery systems.

In an embodiment of the invention, an amount of dry-binder is used to adhere API to bulk sweetener.

In one embodiment of the invention, the flavor may be used as taste masking in chewing gum comprising active ingredients, which by themselves have undesired taste or which alter the taste of the formulation.

The following non-limiting examples illustrate different variations of the present invention. The examples are meant for indicating the inventive concept; hence the mentioned examples should not be understood as exhaustive for the present invention.

EXAMPLES

Example 1

Preparation of Gum Base

The composition of different gum bases are presented in Table 1.

TABLE 1

Gum base matrix compositions. Amounts are given in percent by weight of the gum base matrix.

|  | GB1 | GB2 | GB3 | GB4 |
|---|---|---|---|---|
| Elastomer | 17.5 | 9.8 | 16.0 | 16.0 |
| Polyvinyl acetate | 20.0 | 21.6 | 25.1 | 19.9 |
| Natural resin | 28.0 | 28.3 | 19.4 | 20.1 |
| Filler | 16.5 | 16.6 | 15.0 | 20.5 |
| Emulsifier | 4.0 | 4.2 | 4.4 | 8.9 |
| Softener | 14.0 | 19.4 | 20.0 | 14.6 |
| Antioxidant | 0.05 | 0.1 | 0.1 | 0.0 |

GB = Gum Base

The preparation of gum base is carried out by first adding a high-molecular weight elastomer, polyvinyl acetate, filler to a heated (about 120° C.) and running z-blade mixer. After about twenty minutes of mixing, natural resin is added to the running mixer and mixing is continued for about five minutes followed by addition of further natural resin. After about five minutes of continued mixing, emulsifier and further elastomer are added to the running mixer, and mixing is continued for about five minutes before addition of softener and antioxidant to the running mixer. Mixing is continued for about half an hour to one hour, and the final gum base mass is emptied from the mixer into coated or lined pans, extruded or cast into any desirable shape. Those skilled in the art will recognize that many variations of the above-described procedure may be followed.

Example 2

Preparation of Chewing Gum

In the present example chewing gum is prepared with different types of Carbomer or Carbophil, and chewing gum is prepared without a content of Carbomer or Carbophil.

Carbomer 934, Carbomer 971, Carbomer 974, and Polycarbophil are, respectively, available from B.F. Goodrich as Carbopol®934P NF, Carbopol®971P, Carbopol®974P NF, and Noveon® AA-1.

TABLE 2

Chewing gum compositions. Amounts are given in percent by weight of the chewing gum composition.

|  | CG1 | CG2 | CG3 | CG4 Ref. |
|---|---|---|---|---|
| GB1 | 60 | 60 | 60 | 60 |
| Nicotine polacrilex 15% (~2 mg nicotine per piece) | 1.3 | 1.3 | 1.3 | 1.3 |
| Bulk Sweetener Xylitol | 31.3 | 31.3 | 31.3 | 33.3 |
| Buffer |  |  |  |  |
| Sodium carbonate anhydrous | 2 | 2 | 2 | 2 |
| Sodium bicarbonate | 1 | 1 | 1 | 1 |
| Mint flavour | 2 | 2 | 2 | 2 |
| Intense sweeteners | 0.4 | 0.4 | 0.4 | 0.4 |
| Carbopol 971P | 2 |  |  |  |
| Carbopol 974P |  | 2 |  |  |
| Polycarbophil |  |  | 2 |  |

CG = Chewing Gum

Chewing gums are prepared by use of the gum base GB1 in Example 1 and formulated according to Table 2. A conventional mechanical mixing procedure is used with the use of only moderate heating.

Gum base and filler are mixed in a mixing kettle provided with mixing means like e.g. horizontally placed Z-shaped arms. The kettle had been preheated to a temperature of up to approximately 50 deg. C.

When the content is homogeneous, the other ingredients are added according to a specified time schedule. Nicotine is added in the first half of the mixing process, and Carbopol or Carbophil in powder form is added after nicotine has been added. The pieces evaluated comprise 2 mg nicotine per piece.

The chewing gum can optionally be coated by means of hard coating. The coating may e.g. be applied according to the methods disclosed in the U.S. Pat. No. 6,627,234, hereby included by reference. The pieces evaluated are without coating.

Example 3

In vitro Release

The release rate from chewing gum was carried out according to the procedure set forth in the Ph. Eur. $6^{th}$ ed. 2.9.25, using a phosphate buffer with a pH=7.4, a chewing rate of 60 chew per minute, and with the temperature of the medium at 37° C.

TABLE 3

In vitro measurements of nicotine release from chewing gum compositions.
% nicotine relased of initially added content.

| Time | CG1 | CG2 | CG3 | CG4 Ref. |
|---|---|---|---|---|
| 5 min | 39 | 25 | 26 | 21 |
| 10 min | 84 | 74 | 77 | 32 |
| 20 min | 91 | 89 | 89 | 48 |
| 30 min | 92 | 91 | 91 | 66 |

The results clearly show a significant faster release of nicotine from the formulations containing Carbomers or Carbophil compared to the formulation without Carbomers or Carbophil.

Example 4

Preparation of Chewing Gum

In the present example chewing gum is prepared with varied amounts of Carbomer 974P, and chewing gum is prepared without a content of Carbomer.

TABLE 4

Chewing gum compositions. Amounts are given in percent by weight of the chewing gum composition.

|  | CG5 Ref. | CG6 | CG7 | CG8 | CG9 | CG10 | CG11 |
|---|---|---|---|---|---|---|---|
| GB2 | 60 | 60 | 60 | 60 | 60 | 60 | 60 |
| Nicotine polacrilex 15% (~2 mg nicotine per piece) | 1.36 | 1.36 | 1.36 | 1.36 | 1.36 | 1.36 | 1.36 |
| Bulk Sweetener Xylitol | 33.2 | 33.0 | 32.7 | 32.2 | 31.2 | 29.2 | 28.2 |
| Buffer |  |  |  |  |  |  |  |
| Sodium carbonate anhydrous | 2 | 2 | 2 | 2 | 2 | 2 | 2 |
| Sodium bicarbonate | 1 | 1 | 1 | 1 | 1 | 1 | 1 |
| Mint flavour | 2 | 2 | 2 | 2 | 2 | 2 | 2 |
| Intense sweeteners | 0.4 | 0.4 | 0.4 | 0.4 | 0.4 | 0.4 | 0.4 |
| Carbopol 974P | 0 | 0.2 | 0.5 | 1 | 2 | 4 | 5 |

CG = Chewing Gum

The chewing gum is prepared in the same way as described in Example 2

Example 5

In vitro Release

The release rate from chewing gum was carried out according to the procedure set forth in the Ph. Eur. $6^{th}$ ed. 2.9.25, using a phosphate buffer with a pH=7.4, a chewing rate of 60 chew per minute, and with the temperature of the medium at 37° C.

TABLE 5

In vitro measurements of nicotine release from chewing gum compositions. % nicotine relased of initially added content.

| Time | CG5 Ref. | CG6 | CG7 | CG8 | CG9 | CG10 | CG11 |
|---|---|---|---|---|---|---|---|
| 10 min | 29 | 30 | 33 | 35 | 53 | 82 | 85 |
| 20 min | 50 | 55 | 58 | 74 | 91 | 87 | 92 |
| 30 min | 65 | 70 | 76 | 86 | 94 | 89 | 97 |

The results clearly show the effect of a rising concentration of Carbomer in a chewing gum. At higher concentrations of Carbomer, the faster and more complete release of nicotine is seen. The release rate when using GB2 is in general lower compared to the release rate when using GB1, even for same amount of carbomer. As will be clear to the skilled person, this is due to the influence on the release by the gum base ingredients in question; therefore examples with different gum bases should not be directly compared. In CG11, which comprises 5% by weight of the chewing gum of carbomer, a beginning disintegration was observed.

Example 6

Preparation of Chewing Gum

In the present example chewing gum is prepared with Carbomer 971P, and different gum bases prepared in the same way as described in Example 1.

TABLE 6

Chewing gum compositions. Amounts are given in percent by weight of the chewing gum composition.

|  | CG12 | CG13 | CG14 |
|---|---|---|---|
| GB2 | 60 |  |  |
| GB3 |  | 60 |  |
| GB4 |  |  | 60 |
| Nicotine polacrilex 15% (~2 mg nicotine per piece) | 1.3 | 1.3 | 1.3 |
| Bulk Sweetener Xylitol Buffer | 31.3 | 31.3 | 31.3 |
| Sodium carbonate anhydrous | 2 | 2 | 2 |
| Sodium bicarbonate | 1 | 1 | 1 |
| Mint flavour | 2 | 2 | 2 |
| Intense sweeteners | 0.4 | 0.4 | 0.4 |
| Carbopol 971P | 2 | 2 | 2 |

CG = Chewing Gum

The chewing gum is prepared in the same way as described in Example 2.

Example 7

In vitro Release

The release rate from chewing gum was carried out according to the procedure set forth in the Ph. Eur. 6$^{th}$ ed. 2.9.25, using a phosphate buffer with a pH=7.4, a chewing rate of 60 chew per minute, and with the temperature of the medium at 37° C.

TABLE 7

In vitro measurements of nicotine release from chewing gum compositions. % nicotine released of initially added content

| Time | CG5 Reference | CG12 | CG13 | CG14 |
|---|---|---|---|---|
| 10 min | 32 | 57 | 51 | 54 |

The results clearly show that addition of Carbomer to a nicotine chewing gum results in a faster release.

The addition of inorganic fillers to the bulk portion of the chewing gum composition may increase the release of nicotine further. In a similar way, a change in the average molecular weight of the elastomers may change the nicotine release. In all the examples presented every single raw material within the same example originates from the same lot number.

Example 8

Preparation of Placebo Chewing Gum for Sensory Evaluation

In the present example placebo chewing gum is prepared without nicotine and with varied amounts of Carbomer 974P, and a reference chewing gum is prepared without a content of Carbomer.

TABLE 8

Chewing gum compositions. Amounts are given in percent by weight of the chewing gum composition.

|  | CG15 Reference | CG16 | CG17 | CG18 | CG19 |
|---|---|---|---|---|---|
| GB2 | 60 | 60 | 60 | 60 | 60 |
| Bulk Sweetener Xylitol Buffer | 34.6 | 34.4 | 34.1 | 33.6 | 32.6 |
| Sodium carbonate anhydrous | 2 | 2 | 2 | 2 | 2 |
| Sodium bicarbonate | 1 | 1 | 1 | 1 | 1 |
| Mint flavour | 2 | 2 | 2 | 2 | 2 |
| Intense sweeteners | 0.4 | 0.4 | 0.4 | 0.4 | 0.4 |
| Carbopol 974P | 0 | 0.2 | 0.5 | 1 | 2 |

CG = Chewing Gum

The chewing gum is prepared in the same way as described in Example 2

Example 9

Sensory Evaluation

The chewing gum formulations of Example 8 were tested in a time intensity test by a panel of 9 trained individual test persons and evaluated for Volume.

Volume is evaluated at different points during chewing from zero to fifteen minutes using a scale from 0-15. The sensoric evaluation is defined in scale as follows:

1.5 Little volume 13.5 High volume

Generally a significant difference is observed for Volume. The evaluations at 1, 3, 5 and 10 min for this parameter is presented below.

TABLE 9

Sensory evaluations.

| Volume: | CG15 Reference | CG16 | CG17 | CG18 | CG19 |
|---|---|---|---|---|---|
| 1 min | 6.8 | 6.9 | 6.8 | 6.8 | 6.9 |
| 3 min | 7.1 | 7.3 | 7.2 | 7.4 | 8.2 |
| 5 min | 7.4 | 7.5 | 7.6 | 7.7 | 8.3 |
| 10 min | 7.6 | 7.7 | 7.8 | 7.9 | 8.0 |

It is seen that the volume of the chewing gum increase during chewing, and that the higher the content of Carbomer, the higher volume. The CG19 sample has a very fast growth in volume and the volume is constant after 3 minutes.

The invention claimed is:

1. A chewing gum composition comprising a gum base matrix and a bulk portion, wherein the chewing gum composition comprises nicotine and includes a cross-linked polyacrylic acid added in an amount of 0.1 to 5.0% by weight of the chewing gum composition.

2. The chewing gum composition according to claim 1, wherein the cross-linked polyacrylic acid is added in powder form.

3. The chewing gum composition according to claim 1, wherein the cross-linked polyacrylic acid is added as part of the bulk portion after mixing of the gum base matrix.

4. The chewing gum composition according to claim 1, wherein the cross-linked polyacrylic acid is added in an amount of 0.5 to 3.0% by weight of the chewing gum composition.

5. The chewing gum composition according to claim 1, wherein the percentage of released nicotine after 10 min. in vitro chewing in accordance with Ph. Eur. 2.9.25 in a pH 7.4 phosphate buffer with 60 chews per minute and at a temperature of 37° C. is at least 50% of the initially added content.

6. The chewing gum composition according to claim 1, wherein the percentage of released nicotine after 10 min. in vitro chewing in accordance with Ph. Eur. 2.9.25 in a pH 7.4 phosphate buffer with 60 chews per minute and at a temperature of 37° C. is at least 70% of the initially added content.

7. The chewing gum composition according to claim 1, wherein the gum base matrix constitutes 50 to 80% by weight of the chewing gum composition.

8. The chewing gum composition according to claim 1, wherein the cross-linked polyacrylic acid is a polycarbophil.

9. The chewing gum composition according to claim 1, wherein the cross-linked polyacrylic acid is a carbomer.

10. The chewing gum composition according to claim 9, wherein the carbomer is selected from the group consisting of Carbomer 934, Carbomer 971, Carbomer 974 and mixtures thereof.

11. The chewing gum composition according to claim 1, wherein the cross-linked polyacrylic acid forms a carrier to the nicotine.

12. The chewing gum composition according to claim 1, wherein nicotine is selected from the group consisting of a nicotine salt, the free base form of nicotine, nicotine with a cation exchanger, nicotine polacrilex resin, a nicotine inclusion complex, nicotine bound to zeolites; nicotine bound to cellulose, nicotine bound to microcrystalline microspheres, or nicotine bound to starch microspheres, and mixtures thereof.

13. The chewing gum composition according to claim 1, wherein the nicotine includes a nicotine polacrilex resin.

14. The chewing gum composition according to claim 13, wherein the nicotine consists of nicotine polacrilex resin.

15. The chewing gum composition according to claim 14, wherein the nicotine consists of nicotine polacrilex resin 15%.

16. The chewing gum composition according to claim 1, wherein the nicotine includes a nicotine salt.

17. The chewing gum composition according to claim 16, wherein the nicotine consists of nicotine salt.

18. The chewing gum composition according to claim 1, wherein the nicotine includes a nicotine base.

19. The chewing gum composition according to claim 18, wherein the nicotine consists of the free base form of nicotine.

20. The chewing gum composition according to claim 1, wherein the nicotine is included in a strength of 1 to 5 mg.

21. The chewing gum composition according to claim 1, wherein the addition of cross-linked polyacrylic acid to the chewing gum composition allows for a lower amount of nicotine to be used to deliver the required dose of nicotine to the patient in need thereof as compared to the same chewing gum composition without the addition of the cross-linked polyacrylic acid.

22. The chewing gum composition according to claim 1 comprising a buffer selected from the group consisting of a carbonate, including monocarbonate, bicarbonate or sesquicarbonate, glycerinate, phosphate, glycerophosphate, acetate, glyconate or citrate of an alkali metal, potassium and sodium, trisodium and tripotassium citrate, or ammonium, and mixtures thereof.

23. The chewing gum composition according to claim 22, wherein the amount of buffer is 0.5 to 10% by weight of the chewing gum composition.

24. The chewing gum composition according to claim 1, wherein the gum base matrix comprises an environmentally degradable gum base polymer and nicotine.

25. A method of producing a chewing composition according to claim 1 comprising the steps of providing a gum base matrix and a bulk portion, and adding a cross-linked polyacrylic acid as part of the bulk portion after mixing the gum base matrix.

26. The chewing gum composition according to claim 1, whereby a volume of the chewing gum composition at three minutes is at least 7.2 on a scale of 1.5 to 13.5, as measured by a sensory evaluation panel, with 1.5 meaning little volume and 13.5 meaning high volume.

27. The chewing gum composition according to claim 26, whereby a volume of the chewing gum composition at three minutes is at least 8.2 on a scale of 1.5 to 13.5, as measured by a sensory evaluation panel, with 1.5 meaning little volume and 13.5 meaning high volume.

28. The chewing gum composition according to claim 1, whereby a volume of the chewing gum composition at five minutes is at least 7.5 on a scale of 1.5 to 13.5, as measured by a sensory evaluation panel, with 1.5 meaning little volume and 13.5 meaning high volume.

29. The chewing gum composition according to claim 28, whereby a volume of the chewing gum composition at five minutes is at least 8.3 on a scale of 1.5 to 13.5, as measured by a sensory evaluation panel, with 1.5 meaning little volume and 13.5 meaning high volume.

30. The chewing gum composition according to claim 1, whereby a volume of the chewing gum composition at ten minutes is at least 7.7 on a scale of 1.5 to 13.5, as measured by a sensory evaluation panel, with 1.5 meaning little volume and 13.5 meaning high volume.

31. The chewing gum composition according to claim 30, whereby a volume of the chewing gum composition at ten minutes is at least 8.0 on a scale of 1.5 to 13.5, as measured by a sensory evaluation panel, with 1.5 meaning little volume and 13.5 meaning high volume.

32. The chewing gum composition according to claim 1, wherein the nicotine includes nicotine with a cation exchanger.

33. The chewing gum composition according to claim 1, wherein the nicotine includes a nicotine inclusion complex.

34. The chewing gum composition according to claim 1, wherein the nicotine includes nicotine bound to zeolites; nicotine bound to cellulose, nicotine bound to microcrystalline microspheres, or nicotine bound to starch microspheres, and mixtures thereof.

35. A chewing gum composition comprising a gum base matrix and a bulk portion, wherein the chewing gum composition comprises nicotine and includes a cross-linked polyacrylic acid added in an amount of 0.1 to 5.0% by weight of the chewing gum composition, whereby a volume of the chewing gum composition at three minutes is at least 7.3, at five minutes is as least 7.5 and at ten minutes is at least 7.7, on a scale of 1.5 to 13.5, as measured by a sensory evaluation panel, with 1.5 meaning little volume and 13.5 meaning high volume.

36. The chewing gum composition according to claim 35, whereby a volume of the chewing gum composition at three minutes is at least 8.2, at five minutes is as least 8.3 and at ten minutes is at least 8.0, on a scale of 1.5 to 13.5, as measured by a sensory evaluation panel, with 1.5 meaning little volume and 13.5 meaning high volume.

* * * * *